(12) United States Patent
Wang et al.

(10) Patent No.: US 11,230,469 B2
(45) Date of Patent: Jan. 25, 2022

(54) DRIVE COMPONENT OF A MICRO-NEEDLE SYSTEM AND METHOD FOR DRIVING THE SAME, MICRO-NEEDLE SYSTEM AND METHOD FOR FABRICATING THE SAME

(71) Applicant: BOE Technology Group Co., Ltd., Beijing (CN)

(72) Inventors: Zhidong Wang, Beijing (CN); Lijia Zhou, Beijing (CN); Quanguo Zhou, Beijing (CN); Ronghua Lan, Beijing (CN); Rongjian Yan, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 152 days.

(21) Appl. No.: 16/413,822

(22) Filed: May 16, 2019

(65) Prior Publication Data

US 2020/0071156 A1     Mar. 5, 2020

(30) Foreign Application Priority Data

Aug. 28, 2018 (CN) .......................... 201810987780.1

(51) Int. Cl.
*A61M 37/00*     (2006.01)
*B81B 3/00*     (2006.01)
(Continued)

(52) U.S. Cl.
CPC ....... *B81B 3/0016* (2013.01); *A61M 37/0015* (2013.01); *H01L 41/0986* (2013.01);
(Continued)

(58) Field of Classification Search
CPC ............. B81B 3/0016; A61M 37/0015; A61M 2037/0007; A61M 2037/0023; H01L 41/0986; H01L 41/45
(Continued)

(56) References Cited

U.S. PATENT DOCUMENTS

2003/0117044 A1    6/2003   Urano et al.
2000/3187395    10/2003   Gabel et al.
(Continued)

FOREIGN PATENT DOCUMENTS

CN    102657914 A    9/2012
CN    105902482 A    8/2016
(Continued)

OTHER PUBLICATIONS

Office Action for corresponding Chinese Application 201810987780.1 dated Jul. 13, 2020.
(Continued)

*Primary Examiner* — Phillip A Gray
(74) *Attorney, Agent, or Firm* — Arent Fox LLP; Michael Fainberg

(57) ABSTRACT

The disclosure discloses a drive component of a micro-needle system, a method for driving the same, a micro-needle system and a method for fabricating the same; wherein the drive component includes a substrate with a groove; a bottom electrode in the groove; an electro-active polymer layer, covering the bottom electrode, in the groove; and an upper flexible electrode covering the electro-active polymer layer; wherein the upper flexible electrode and the bottom electrode are configured to generate a voltage, and the electro-active polymer layer is configured to generate a strain under the voltage.

20 Claims, 13 Drawing Sheets

(51) Int. Cl.
    *H01L 41/09*     (2006.01)
    *H01L 41/45*     (2013.01)
    *H01L 41/193*     (2006.01)

(52) U.S. Cl.
    CPC ....... *H01L 41/45* (2013.01); *A61M 2037/003* (2013.01); *A61M 2037/0007* (2013.01); *A61M 2037/0023* (2013.01); *A61M 2037/0053* (2013.01); *A61M 2037/0061* (2013.01); *A61M 2205/0283* (2013.01); *B81B 2201/055* (2013.01); *H01L 41/193* (2013.01)

(58) Field of Classification Search
    USPC .......................................................... 604/46
    See application file for complete search history.

(56) References Cited

U.S. PATENT DOCUMENTS

| | | |
|---|---|---|
| 2010/0130910 A1 | 5/2010 | Berenson |
| 2016/0058342 A1* | 3/2016 | Maiz-Aguinaga ..... A61B 5/685<br>600/345 |

FOREIGN PATENT DOCUMENTS

| | | |
|---|---|---|
| EP | 1973479 B1 | 9/2016 |
| JP | 2001-263486 A | 9/2001 |
| JP | 2016067723 A | 5/2016 |
| KR | 20080079755 A | 9/2008 |

OTHER PUBLICATIONS

Notification of Third Chinese Office Action issued in related Application No. 201810987780.1 dated Jun. 9, 2021.

\* cited by examiner

--Prior Art--

DRIVE COMPONENT OF A MICRO-NEEDLE SYSTEM AND METHOD FOR DRIVING THE SAME, MICRO-NEEDLE SYSTEM AND METHOD FOR FABRICATING THE SAME

CROSS-REFERENCE TO RELATED APPLICATION

This application claims priority to Chinese Patent Application No. 201810987780.1, filed on Aug. 28, 2018, the content of which is incorporated by reference in the entirety.

TECHNICAL FIELD

This disclosure relates to the field of biomedical technologies, and particularly to a drive component of a micro-needle system, a method for driving the same, a micro-needle system and a method for fabricating the same.

DESCRIPTION OF THE RELATED ART

A bio-micro-electro-mechanical system (Bio-MEMS) is a technology that applies an MEMS technology to a biomedical field. Where, a micro-needle system is an important research point of the Bio-MEMS, and is well applied in the injection of insulin or the like; and MEMS devices, such as the micro-needle system, can be used to control the rate, concentration, and time of the drug release, and the part of the human body where the drug is released, so that an effective concentration of an active agent in the system may be maintained for a certain period of time.

SUMMARY

Embodiments of the disclosure provide a drive component of a micro-needle system, a method for driving the same, a micro-needle system and a method for fabricating the same.

In an aspect, the embodiments of the disclosure provide a drive component of a micro-needle system, including: a substrate with a groove; a bottom electrode in the groove; an electro-active polymer layer, covering the bottom electrode, in the groove; and an upper flexible electrode covering the electro-active polymer layer; wherein the upper flexible electrode and the bottom electrode are configured to generate a voltage, and the electro-active polymer layer is configured to generate a strain under the voltage.

In some embodiments, the groove is arranged with one bottom electrode or a plurality of bottom electrodes arranged spaced apart from each other.

In some embodiments, the upper flexible electrode only covers the groove, or covers an entire surface of the substrate.

In some embodiments, the upper flexible electrode is flush with an upper surface of the groove or is lower than the upper surface of the groove.

In some embodiments, a material of the electro-active polymer layer includes a conductive polymer.

In some embodiments, a material of the electro-active polymer layer includes an ionic polymer-based metal composite.

In another aspect, the embodiments of the disclosure further provide a micro-needle system, including a micro-needle component and a drive component fit tightly with each other; wherein the micro-needle component includes a plurality of micro-needle protrusions, each of which includes a micro-needle through-hole; the drive component includes a substrate with a groove, a bottom electrode in the groove, an electro-active polymer layer covering the bottom electrode in the groove, and an upper flexible electrode covering the electro-active polymer layer; wherein the upper flexible electrode and the bottom electrode are configured to generate a voltage, and the electro-active polymer layer is configured to generate a strain under the voltage; and a liquid storage region is arranged between respective micro-needle through-holes of the micro-needle component and the groove of the drive component.

In some embodiments, the micro-needle system includes one liquid storage region connecting with the respective micro-needle through-holes, or a plurality of liquid storage regions corresponding to and connected with the respective micro-needle through-holes in a one-to-one manner.

In some embodiments, the drive component includes one or a plurality of grooves; and the upper flexible electrode is adjacent to the liquid storage region.

In some embodiments, each groove is arranged with one bottom electrode, or a plurality of bottom electrodes arranged spaced apart from each other.

In some embodiments, when the drive component includes the plurality of grooves, the upper flexible electrode is arranged as a whole layer to cover each electro-active polymer layer in the plurality of grooves.

In some embodiments, the upper flexible electrode only covers the groove, or covers an entire surface of the substrate.

In some embodiments, the upper flexible electrode is flush with an upper surface of the groove or is lower than the upper surface of the groove.

In some embodiments, a material of the electro-active polymer layer includes a conductive polymer.

In some embodiments, a material of the electro-active polymer layer includes an ionic polymer-based metal composite.

In some embodiments, the micro-needle component is arranged with a groove on a side facing the drive component, and the liquid storage region includes the groove of the micro-needle component.

In still another aspect, the embodiments of the disclosure further provide a method for driving the drive component according to the embodiments of the disclosure, including: applying an electrical signal to the upper flexible electrode and the bottom electrode to generate a voltage to make the electro-active polymer layer generate a strain under the voltage.

In some embodiments, when a material of the electro-active polymer layer is a conductive polymer, a value of the voltage ranges from 1.2V to 10V; or when a material of the electro-active polymer layer is an ionic polymer-based metal composite, a value of the voltage ranges from 1V to 7V.

In yet another aspect, the embodiments of the disclosure further provide a method for fabricating the micro-needle system according to the embodiments of the disclosure, including: forming the plurality of micro-needle protrusions on a side of a substrate of the micro-needle component via an etching process, and forming respective micro-needle through-holes at positions of the plurality of micro-needle protrusions via an ion etching process; forming the groove on the substrate of the drive component via an etching process, and forming the bottom electrode, the electro-active polymer layer and the upper flexible electrode sequentially in the groove of the drive component; and bonding the micro-needle component and the drive component via a bonding process to form the micro-needle system.

In some embodiments, the method further includes: forming the liquid storage region on the other side of the substrate of the micro-needle component via an etching process.

BRIEF DESCRIPTION OF THE DRAWINGS

In order to make the technical solutions according to the embodiments of the disclosure more apparent, the drawings to which a description of the embodiments refers will be briefly introduced below, and apparently the drawings to be described below are merely illustrative of some of the embodiments of the disclosure, and those ordinarily skilled in the art can derive from these drawings other drawings without any inventive effort.

DETAILED DESCRIPTION OF THE EMBODIMENTS

Figure 1:
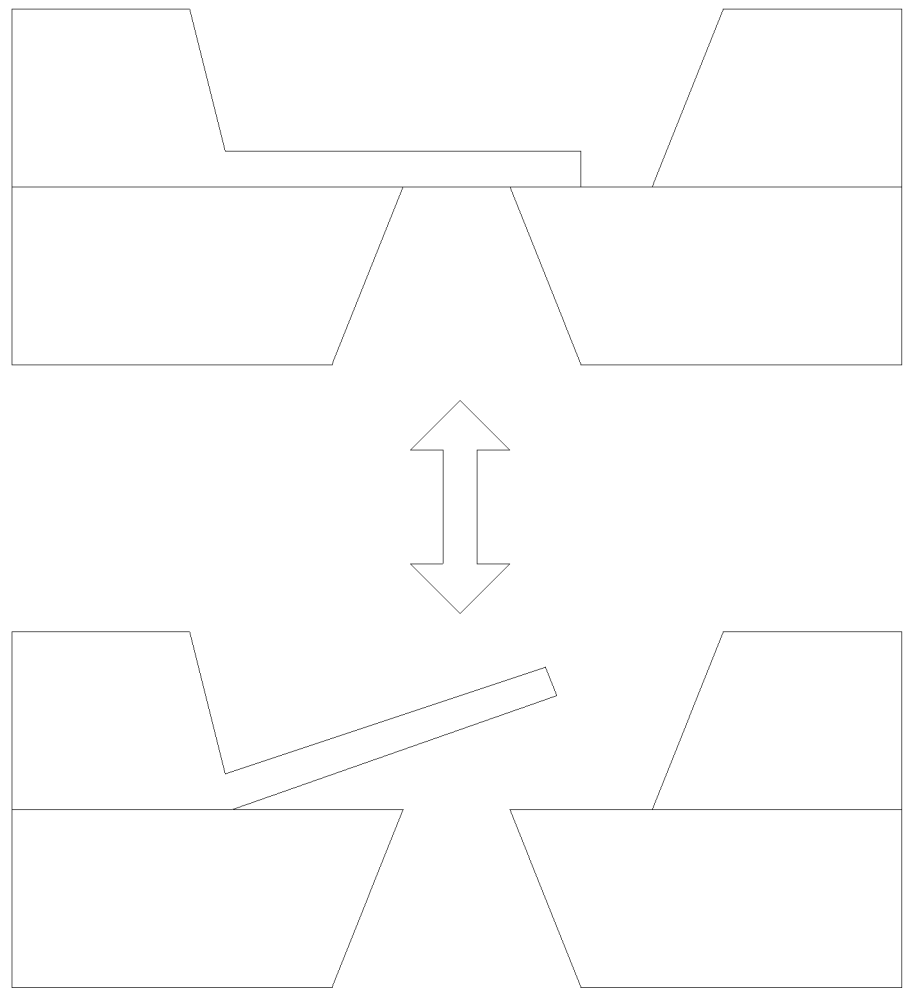
FIG. 1 is a schematic diagram of a cantilever-beam-type micro-valve in the related art in an open state and a closed state.
Figure 2:
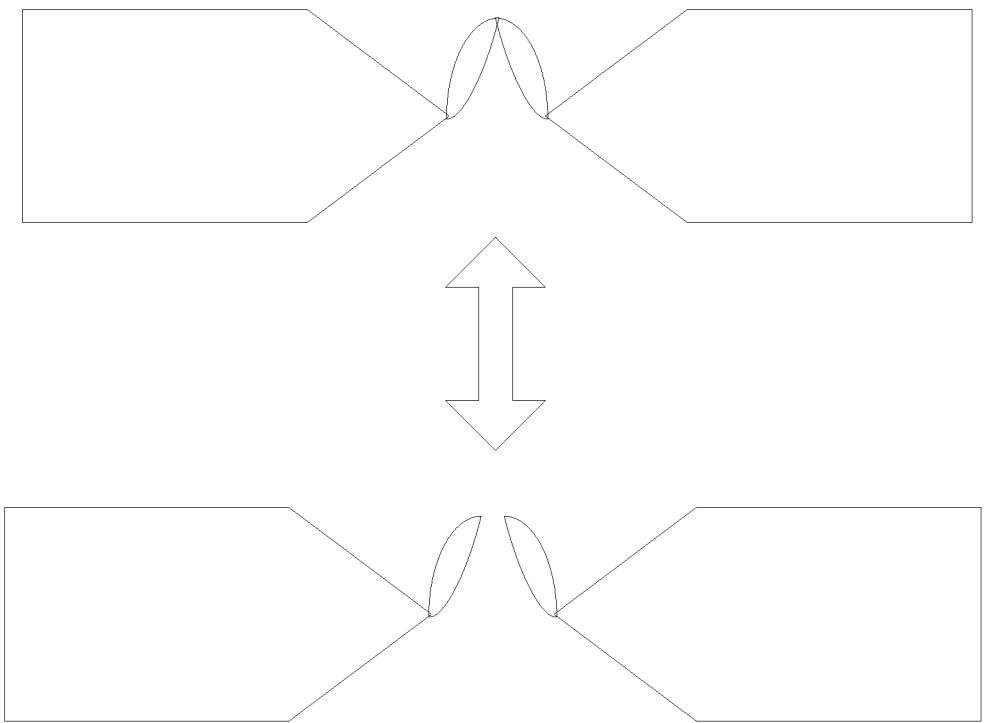
FIG. 2 is a schematic diagram of a V-type valve in the related art in an open state and a closed state.

A micro-needle system in the related art generally adopts a structure, such as a mechanical micro-pump, a mechanical micro-valve, or the like, as a driver. For example, FIG. 1 illustrates a schematic diagram of a cantilever-beam-type micro-valve in the related art in an open state and a closed state, and FIG. 2 illustrates a schematic diagram of a V-type valve in the related art in an open state and a closed state. Where MEMS devices, such as the cantilever-beam-type micro-valve, may be in firm contact with a substrate easily due to effects of electrostatic force, hydrogen bonding, Van Der Waals force and the like, thereby causing malfunction of the micro-needle system.

In order to make the objects, technical solutions, and advantages of the embodiments of the disclosure more apparent, the technical solutions according to the embodiments of the disclosure will be described below clearly and fully with reference to the drawings in the embodiments of the disclosure, and apparently the embodiments described below are only a part but not all of the embodiments of the disclosure. Based upon the embodiments here of the disclosure, all the other embodiments which can occur to those skilled in the art without any inventive effort shall fall into the scope of the disclosure.

The shapes and sizes of respective components in the drawings do not reflect the actual proportions, and are merely intended to illustrate the content of the disclosure.

As illustrated in FIG. 3A to FIG. 3D, a drive component of a micro-needle system is provided in the embodiments of the disclosure, where the drive component includes: a substrate 110 with a groove 111; a bottom electrode 120 in the groove 111; an electro-active polymer layer 130, covering the bottom electrode 120, in the groove 111; and an upper flexible electrode 140 covering the electro-active polymer layer 130; where the upper flexible electrode 140 and the bottom electrode 120 are configured to generate a voltage, and the electro-active polymer layer 130 is configured to generate a strain under the voltage.

In the drive component above according to the embodiments of the disclosure, since an electro-active polymer material may generate a strain upon application of voltage, the electro-active polymer layer 130 and the bottom electrode 120 are arranged in the groove 111 of the substrate 110, and the electro-active polymer layer 130 is controlled by the voltage to generate a deformation to thereby change a shape of the upper flexible electrode 140 covering the electro-active polymer layer 130 and thus squeeze liquid in a liquid storage region into a micro-needle through-hole when the drive component is applied to a micro-needle system, thereby achieving the effect of driving the liquid into human skin by a driver, such as a micro-pump or a micro-valve, in the related art. And since the driving is achieved by controlling the electro-active polymer material to generate a deformation under the voltage, the problem in the related art that the MEMS devices, such as the cantilever-beam-type micro-valve, may be in firm contact with the substrate easily due to effects of electrostatic force, hydrogen bonding, Van Der Waals force and the like, thereby causing malfunction of the micro-needle system, can be avoided.

In some embodiments, in the drive component according to the embodiments of the disclosure, a material of the electro-active polymer layer 130 includes a conductive polymer, or an ionic polymer-based metal composite, etc., and all these materials have the property of being deformed under control of the voltage.

In some embodiments, the conductive polymer material has a typical drive voltage of 1.2V, a maximum drive voltage of 10V, a typical amount of deformation of 2%, and a maximum amount of deformation of 12%; and the ionic polymer-based metal composite material has a typical drive voltage of 1~7V, and a maximum amount of deformation of 10%.

Figure 3A:
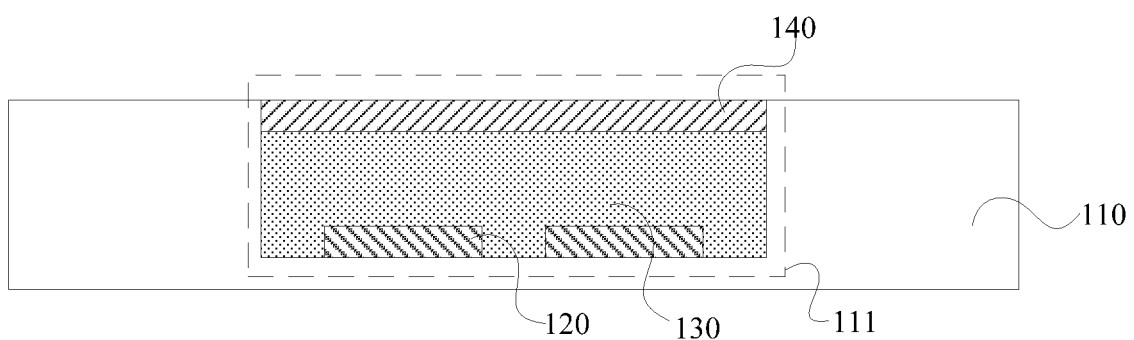
FIG. 3A to FIG. 3D are schematic structural diagrams of a drive component of a micro-needle system according to the embodiments of the disclosure.
Figure 4A:
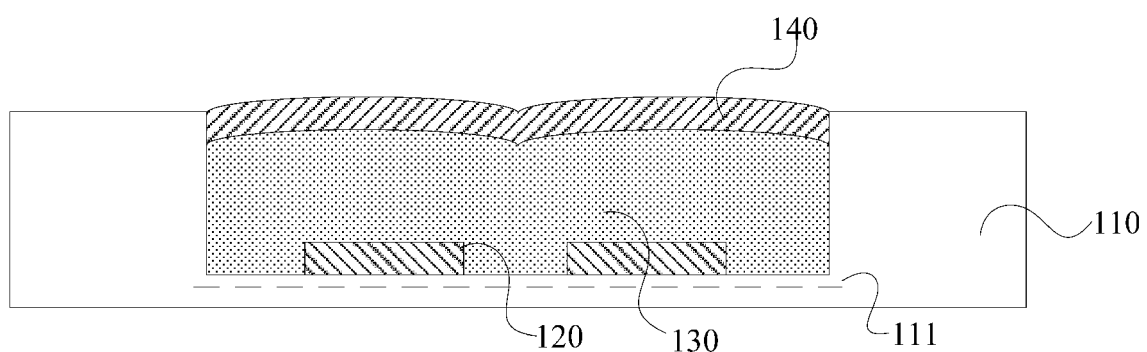
FIG. 4A to FIG. 4B are schematic structural diagrams of a drive component in a working state according to the embodiments of the disclosure.
Figure 4B:
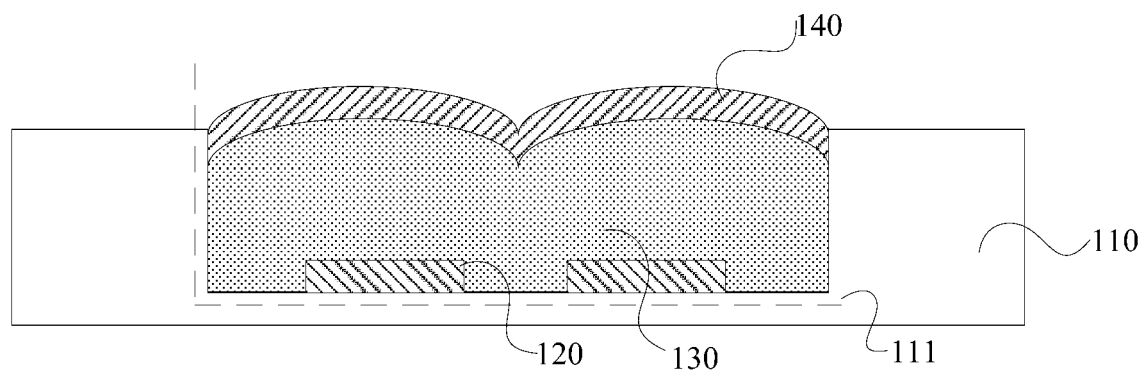

In some embodiments, by taking the drive component illustrated in FIG. 3A as an example, when the drive component is in a non-working state, no voltage is applied to the upper flexible electrode 140 and the bottom electrode 120, and at this time, there is no strain in the electro-active polymer layer 130 and the electro-active polymer layer 130 is in a flat state, therefore, no liquid will be driven into a micro-needle through-hole to thereby enter the human skin. And as illustrated in FIG. 4A, when the drive component is in a working state, a voltage is applied to the upper flexible electrode 140 and the bottom electrode 120, at this time, the electro-active polymer layer 130 may generate a strain and form a protrusion to thereby squeeze the liquid in the liquid storage region to enter the human skin via the micro-needle through-hole. For example, as illustrated in FIG. 4B, as the voltage applied to the upper flexible electrode 140 and the bottom electrode 120 increases, the strain in the electro-active polymer layer 130 becomes larger and the protrusion formed thereof becomes more obvious, thereby the liquid in the liquid storage region will be squeezed to enter the human skin via the micro-needle through-hole continuously.

In some embodiments, in the drive component according to the embodiments of the disclosure, a glass can be selected as the substrate 110, and the groove can be formed on the glass; or a resin material, such as Polydimethylsiloxan (PDMS) or the like, can be selected as the substrate 110, which will not be limited herein. Further, the upper flexible electrode 140 and the bottom electrode 120 can be made of a conductive material such as indium tin oxide, or can be made of another conductive material, which will not be limited herein.

Figure 3B:
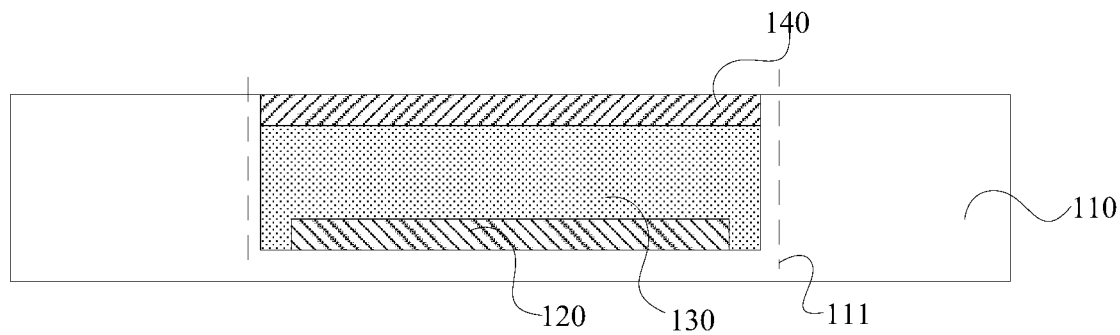
Figure 3C:
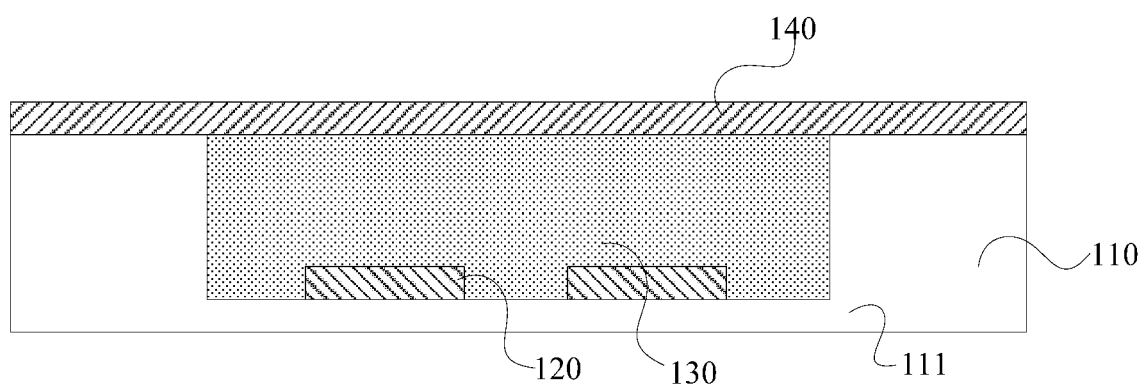
Figure 3D:
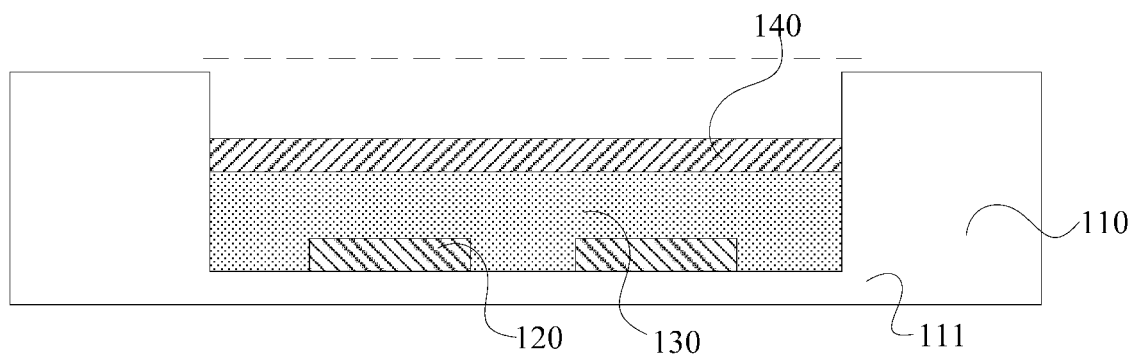

In some embodiments, in the drive component according to the embodiments of the disclosure, there can be a plurality of bottom electrodes 120 arranged spaced apart from each other as illustrated in FIG. 3A, FIG. 3C, and FIG. 3D, or there can be only one bottom electrode 120 as illustrated in FIG. 3B, which will not be limited herein.

In some embodiments, in the drive component according to the embodiments of the disclosure, the groove 111 is arranged with one bottom electrode 120, and the one bottom electrode 120 covers a bottom of the groove 111 to thereby simplify the manufacturing process. Further, the groove 111 can alternatively be arranged with a plurality of bottom electrodes 120, and when the plurality of bottom electrodes 120 are arranged in the groove 111, the amount of deformation of the electro-active polymer layer 130 can be finely controlled by driving the bottom electrodes 120 one by one, thereby accurately controlling the liquid amount entering the micro-needle through-hole.

In some embodiments, in the drive component according to the embodiments of the disclosure, the upper flexible electrode 140 can only cover the groove 111 as illustrated in FIG. 3A, FIG. 3B, and FIG. 3D, that is, the upper flexible electrode 140 is located inside the groove 111. Or, as illustrated in FIG. 3C, the upper flexible electrode 140 can alternatively cover an entire surface of the substrate 110, which will not be limited herein.

In some embodiments, in the drive component according to the embodiments of the disclosure, the upper flexible electrode 140 can be flush with an upper surface of the groove 111 as illustrated in FIG. 3A to FIG. 3C. Or, as illustrated in FIG. 3D, the upper flexible electrode 140 can also be lower than the upper surface of the groove 111, so that the groove 111 forms a part of the liquid storage region above the upper flexible electrode 140, thereby omitting the process of separately manufacturing the liquid storage region.

Based upon the same inventive concept, the embodiments of the disclosure further provide a method for driving the drive component above according to the embodiments of the disclosure, where the method includes: applying an electrical signal to the upper flexible electrode 140 and the bottom electrode 120 to generate a voltage, so that as illustrated in FIG. 4A and FIG. 4B, the electro-active polymer layer 130 may undergo strain upon application of the voltage, and the shape of the upper flexible electrode 140 covering the electro-active polymer layer 130 may be changed to squeeze the liquid in the liquid storage region into the micro-needle through-hole when the drive component is applied to the micro-needle system, thereby achieving the effect of driving the liquid into human skin by a driver, such as a micro-pump or a micro-valve, in the related art. And since the driving is achieved by controlling the electro-active polymer material to generate a deformation under the voltage, the problem in the related art that the MEMS devices, such as the cantilever-beam-type micro-valve, may be in firm contact with the substrate easily due to effects of electrostatic force, hydrogen bonding, Van Der Waals force and the like, thereby causing malfunction of the micro-needle system, can be avoided.

In some embodiments, a magnitude of the electrical signal applied to the upper flexible electrode 140 and the bottom electrode 120 can be determined according to the material of the electro-active polymer layer 130. For example, if the material of the electro-active polymer layer 130 is a conductive polymer, a drive voltage of the electro-active polymer layer can be 1.2V~10V, where 1.2V is a typical drive voltage value and 10V is a maximum drive voltage value thereof, and an amount of deformation of the electro-active polymer layer can be 2% to 12%, where 2% is a typical amount of deformation and 12% is a maximum amount of deformation thereof; and if the material of the electro-active polymer layer 130 is an ionic polymer-based metal composite, a typical drive voltage of the electro-active polymer layer can be 1~7V, and a maximum amount of deformation of the electro-active polymer layer can be 10%. In addition, the electrical signal applied to the upper flexible electrode 140 and the bottom electrode 120 can be increased gradually based upon a fixed value to ensure that the electro-active polymer layer 130 can have a continuous amount of deformation, as illustrated in FIG. 4A and FIG. 4B.

In some embodiments, in the method for driving the drive component above according to the embodiments of the disclosure, when there are a plurality of bottom electrodes 120 in the groove, a strain amount of the electro-active polymer layer can be controlled by adjusting the number of the bottom electrodes applied with the electrical signal and the amplitude of the electrical signal, thereby accurately controlling the liquid amount entering the micro-needle through-hole. For example, in an initial stage, a certain bottom electrode 120 can be applied with an electrical signal from small to large, so that a continuous amount of deformation may occur at a corresponding position of the electro-active polymer layer 130; in a subsequent stage, when a maximum value of the electrical signal applied to the certain bottom electrode 120 is maintained, another bottom electrode 120 is applied with an electrical signal from small to large, so that a continuous amount of deformation occurs at a corresponding position of the electro-active polymer layer 130; and the above process is performed similarly until all the bottom electrodes 120 are applied with an electrical signal with the maximum value.

Figure 5A:
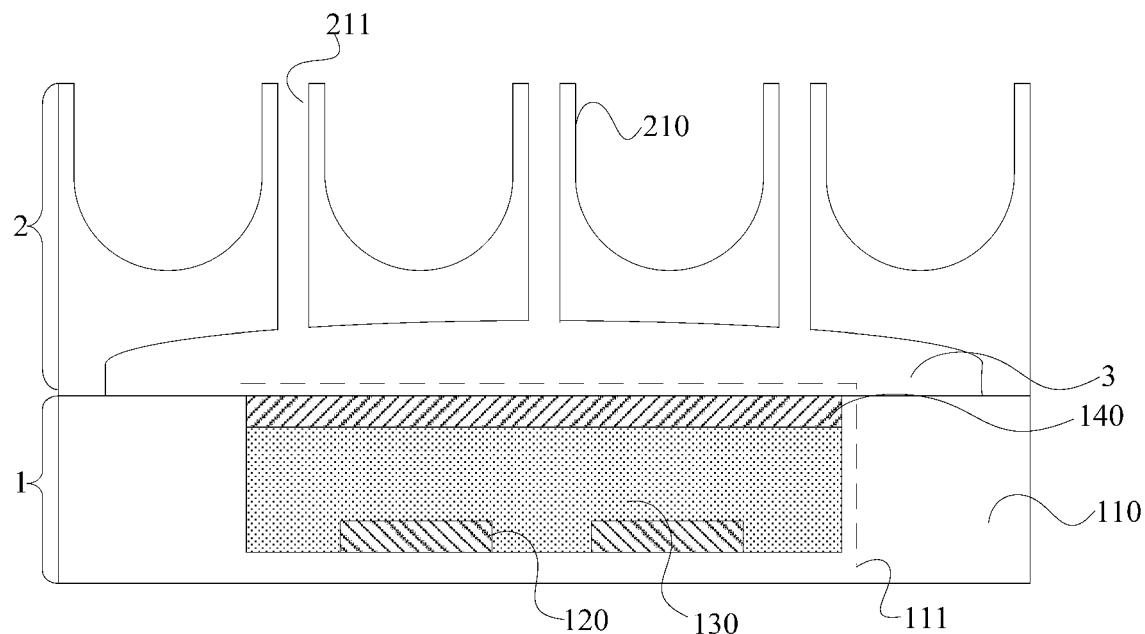
FIG. 5A to FIG. 5G are schematic structural diagrams of a micro-needle system according to the embodiments of the disclosure.

Based upon the same inventive concept, the embodiments of the disclosure further provide a micro-needle system, and as illustrated in FIG. 5A to FIG. 5Q the micro-needle system includes a micro-needle component 2 and a drive component 1 fit tightly with each other. Where the micro-needle component 2 includes a plurality of micro-needle protrusions 210, each of which includes a micro-needle through-hole 211. The drive component 1 includes a substrate 110 with a groove 111; a bottom electrode 120 in the groove 111; an electro-active polymer layer 130, covering the bottom electrode 120, in the groove 111; and an upper flexible electrode 140 covering the electro-active polymer layer 130; where the upper flexible electrode 140 and the bottom electrode 120 are configured to generate a voltage, and the electro-active polymer layer 130 is configured to generate a strain under the voltage. Where a liquid storage region 3 is arranged between respective micro-needle through-holes 211 of the micro-needle component 2 and the groove 111 of the drive component 1.

In some embodiments, in the micro-needle system above according to the embodiments of the disclosure, since the electro-active polymer material may generate a strain upon application of voltage, the electro-active polymer layer 130 and the bottom electrode 120 are arranged in the groove 111 of the substrate 110 of the drive component 1, and the electro-active polymer layer 130 is controlled by the voltage to generate a deformation to thereby change the shape of the upper flexible electrode 140 covering the electro-active polymer layer 130 and thus squeeze liquid in the liquid storage region 3 into the micro-needle through-holes 211 of the micro-needle component 2, thereby achieving the effect of driving the liquid into human skin by a driver, such as a micro-pump or a micro-valve, in the related art. And since the driving is achieved by controlling the electro-active polymer material to generate a deformation under the voltage, the problem in the related art that the MEMS devices, such as the cantilever-beam-type micro-valve, may be in firm contact with the substrate easily due to effects of electrostatic force, hydrogen bonding, Van Der Waals force and the like, thereby causing malfunction of the micro-needle system, can be avoided.

In some embodiments, in the micro-needle system above according to the embodiments of the disclosure, a glass can be selected as the substrate 110, and the groove can be formed on the glass; or a resin material, such as PDMS or the like, can be selected as the substrate 110, which will not be limited herein. Further, the upper flexible electrode 140 and the bottom electrode 120 can be made of a conductive material such as indium tin oxide, or can be made of another conductive material, which will not be limited herein; and the micro-needle component 2 can be made of silica gel, which will not be limited herein.

Figure 5B:
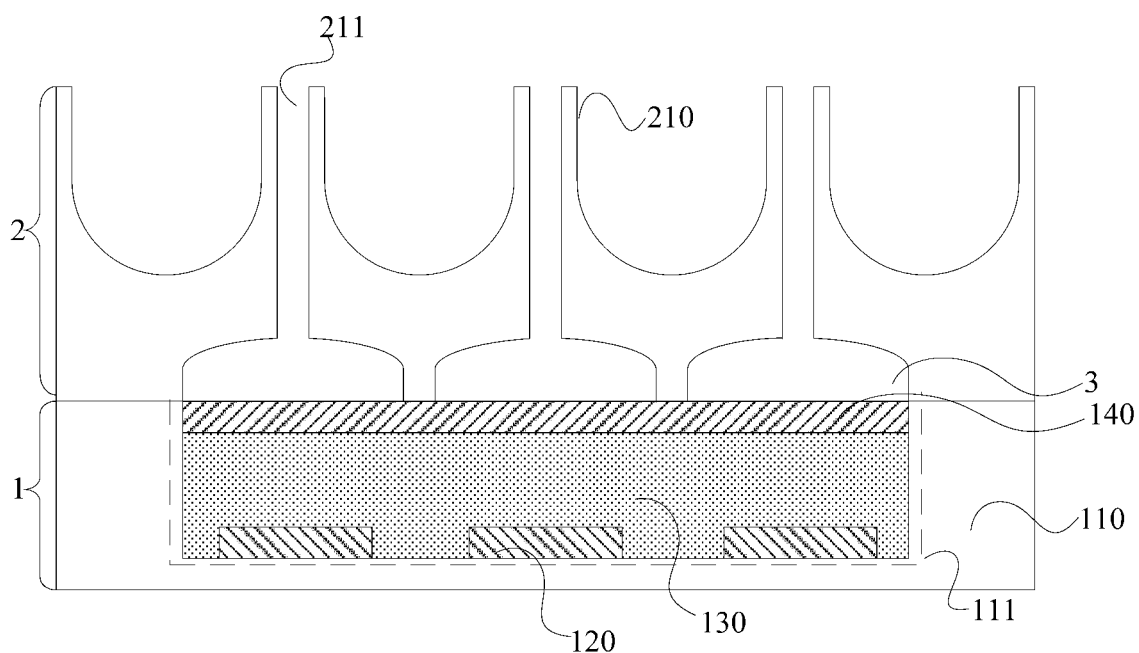
Figure 5C:
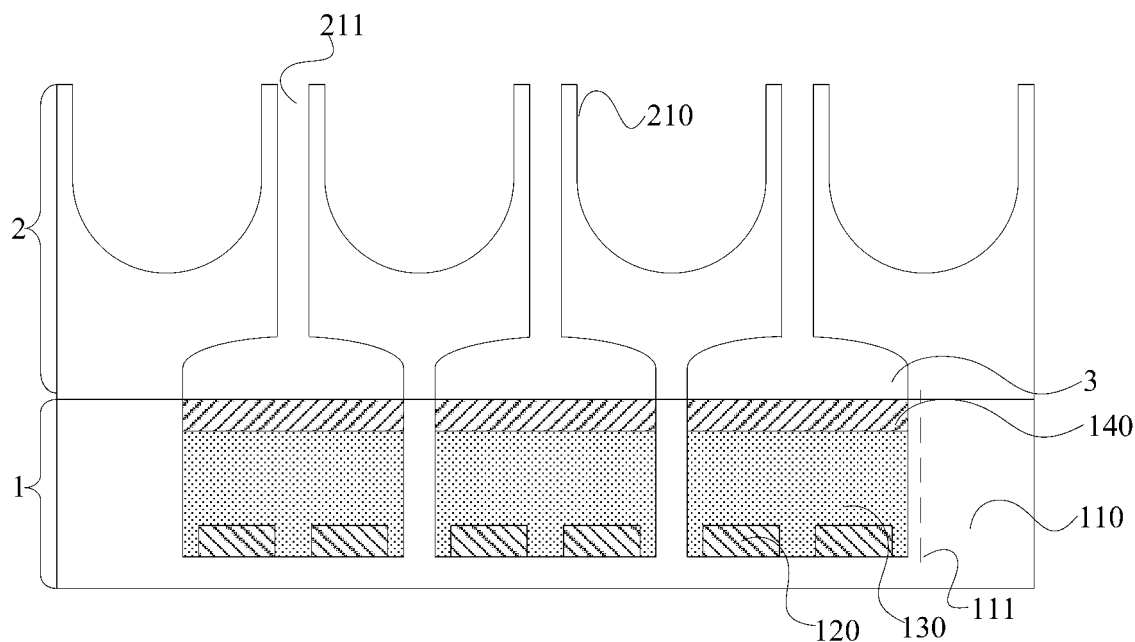

In some embodiments, in the micro-needle system above according to the embodiments of the disclosure, as illustrated in FIG. 5A, and FIG. 5D to FIG. 5G there can be one liquid storage region 3 that connects with the respective micro-needle through-holes 211; that is, the liquid is supplied to the respective micro-needle through-holes 211 via a common liquid storage region 3 to thereby facilitate the manufacturing of the liquid storage region 3. Or, as illustrated in FIG. 5B and FIG. 5C, there can be a plurality of liquid storage regions 3 corresponding to the respective micro-needle through-holes 211 in a one-to-one manner, and each liquid storage region 3 can connect with a corresponding micro-needle through-hole 211, that is, by supplying the liquid to corresponding micro-needle through-holes 211 via liquid storage regions 3 that are independent from one another, the liquid amount entering each micro-needle through-hole 211 can be precisely controlled.

Figure 5D:
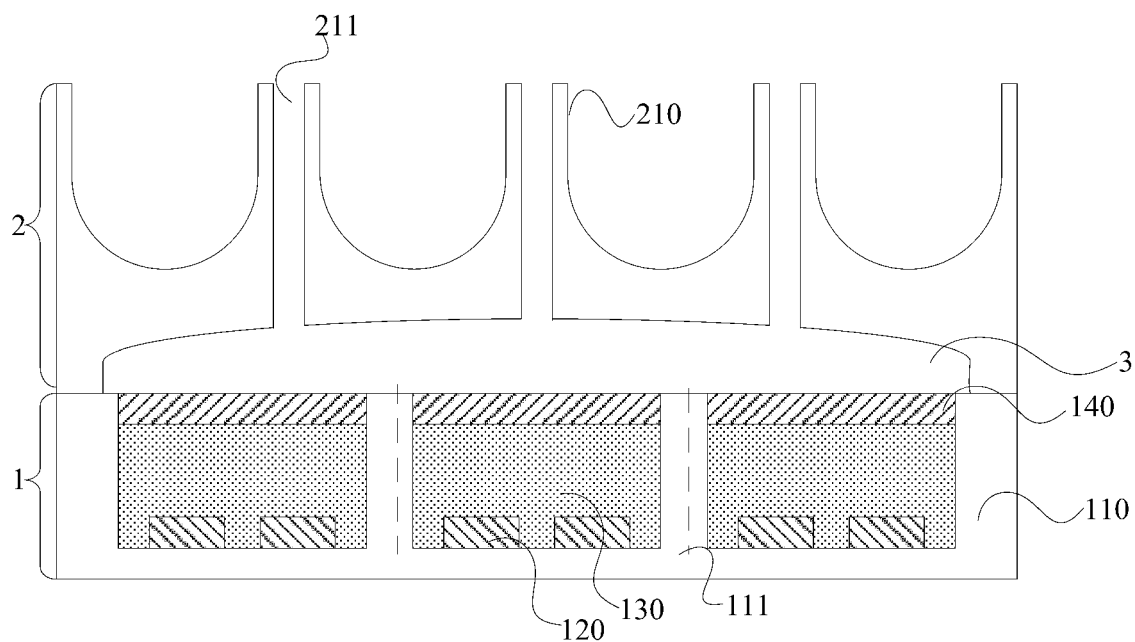

In some embodiments, in the micro-needle system above according to the embodiments of the disclosure, there can be one groove 111 as illustrated in FIG. 5A, FIG. 5B, FIG. 5F, and FIG. 5G; that is, the liquid storage region 3 controls the liquid amount entering each micro-needle through-hole 211 by a deformation of the electro-active polymer layer 130 in one groove 111. Or, as illustrated in FIG. 5C to FIG. 5E, there can be a plurality of grooves 111 arranged in a one-to-one correspondence manner with the respective micro-needle through-holes 211 to accurately control the liquid amount entering each micro-needle through-hole 211, and the upper flexible electrodes (s) 140 is or are adjacent to the liquid storage region (s) 3.

In some embodiments, in the micro-needle system above according to the embodiments of the disclosure, as illustrated in FIG. 5A to FIG. 5G there can be a plurality of bottom electrodes 120 arranged spaced apart from each other in one groove 111, or there can be only one bottom electrode 120 in one groove 111, which will not be limited herein. Where, when a groove 111 is arranged with one bottom electrode 120, the one bottom electrode 120 can cover a bottom of the groove 111 to thereby simplify the manufacturing process; and when a groove 111 is arranged with a plurality of bottom electrodes 120, the amount of deformation of the electro-active polymer layer 130 can be finely controlled by driving the bottom electrodes 120 one by one, thereby accurately controlling the liquid amount entering each micro-needle through-hole.

Figure 5E:
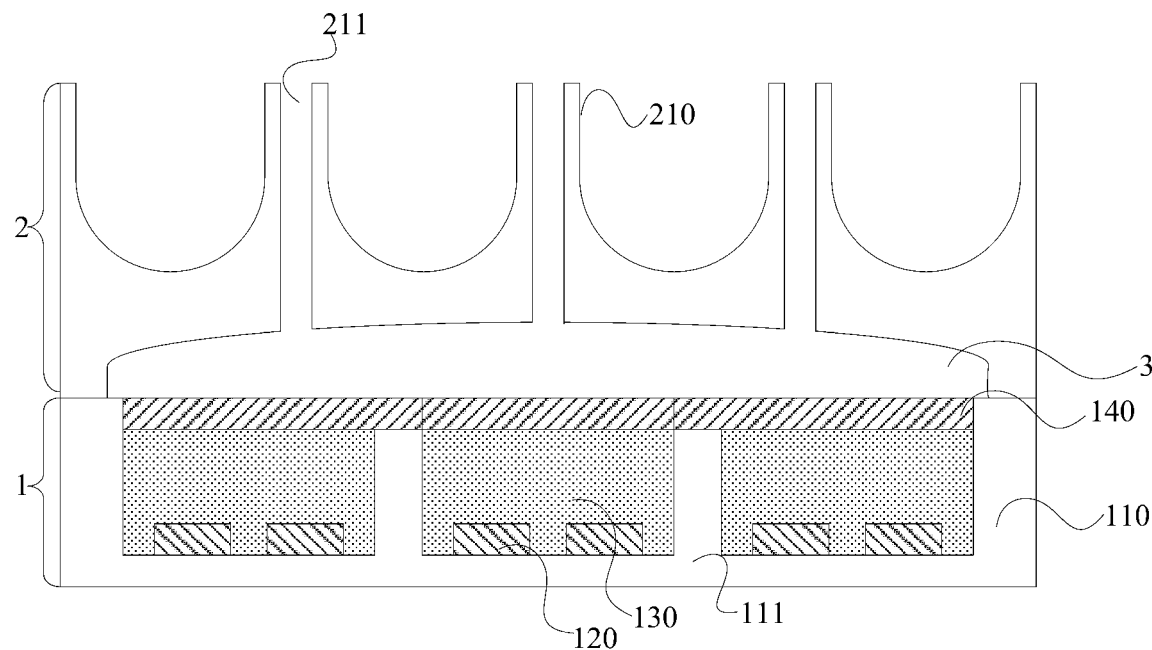

In some embodiments, in the micro-needle system above according to the embodiments of the disclosure, as illustrated in FIG. 5E, if there is a plurality of grooves 111, the upper flexible electrode 140, covering each electro-active polymer layer 130 in the plurality of grooves 111, can be arranged as a whole layer to simplify the process of manufacturing the upper flexible electrode 140.

Or, in some embodiments, in the micro-needle system above according to the embodiments of the disclosure, each upper flexible electrode 140 can only cover a corresponding groove 111 as illustrated in FIG. 5A to FIG. 5D, FIG. 5F, and FIG. 5G; that is, each upper flexible electrode 140 is located inside the corresponding groove 111.

Figure 5F:
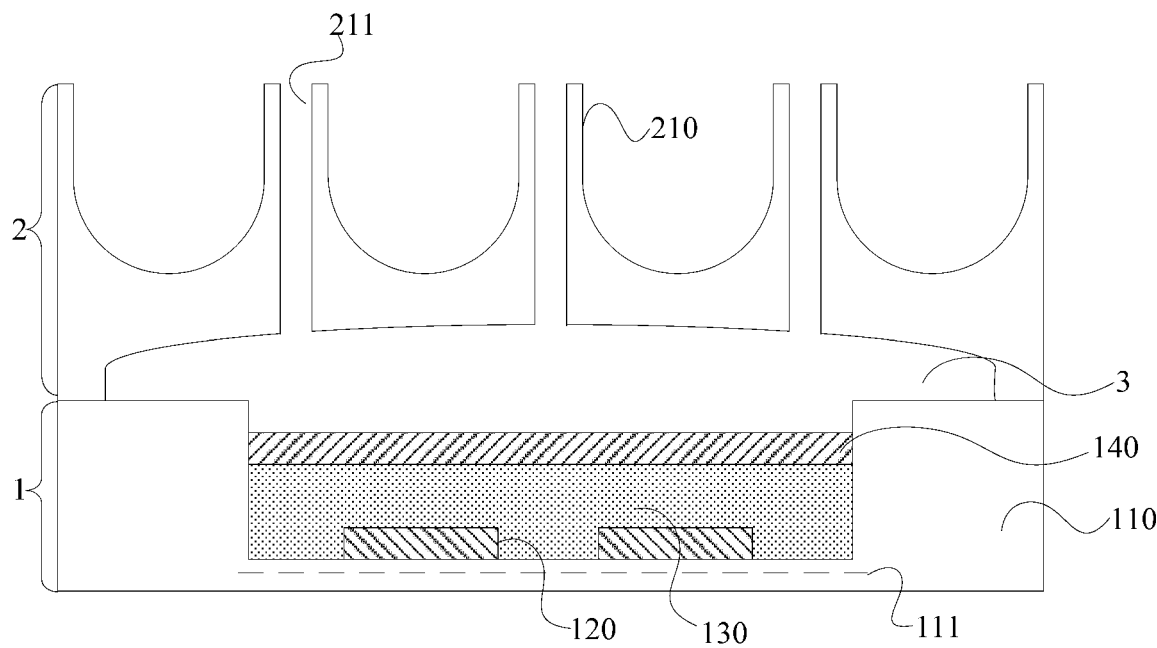
Figure 5G:
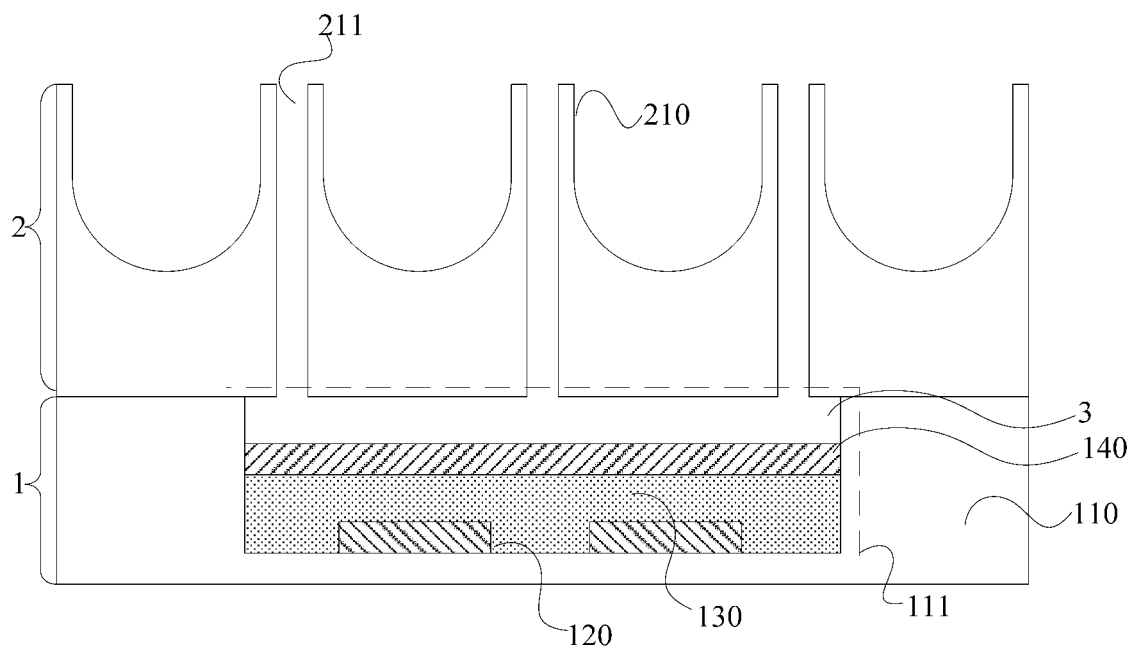

In some embodiments, in the micro-needle system above according to the embodiments of the disclosure, each upper flexible electrode 140 can be flush with an upper surface of a corresponding groove 111 as illustrated in FIG. 5A to FIG. 5E. Or, as illustrated in FIG. 5F to FIG. 5G each upper flexible electrode 140 can be lower than the upper surface of the corresponding groove 111, so that the corresponding groove 111 can form a part of a liquid storage region above the upper flexible electrode 140, thereby omitting or simplifying the process of separately manufacturing the liquid storage region.

In some embodiments, in the micro-needle system above according to the embodiments of the disclosure, a material of each electro-active polymer layer 130 can include a conductive polymer, or an ionic polymer-based metal composite, etc., and all these materials have the property of being deformed under control of the voltage.

In some embodiments, the conductive polymer material has a typical drive voltage of 1.2V, a maximum drive voltage of 10V, a typical amount of deformation of 2%, and a maximum amount of deformation of 12%; and the ionic polymer-based metal composite material has a typical drive voltage of 1~7V, and a maximum amount of deformation of 10%.

Figure 6A:
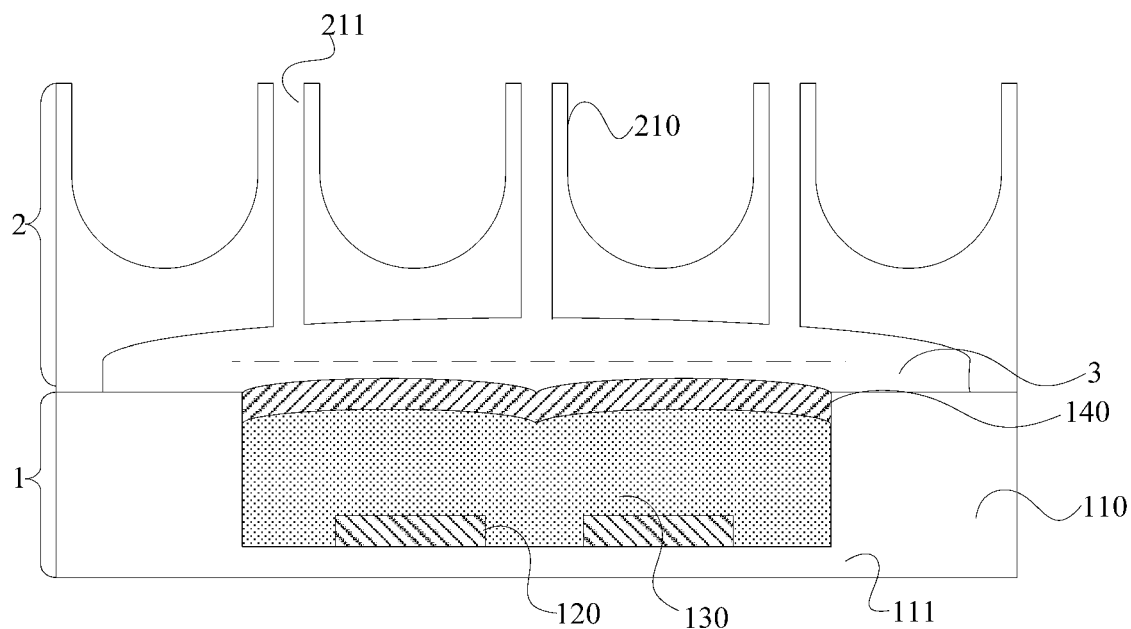
FIG. 6A to FIG. 6B are schematic diagrams of a micro-needle system in a working state according to the embodiments of the disclosure.
Figure 6B:
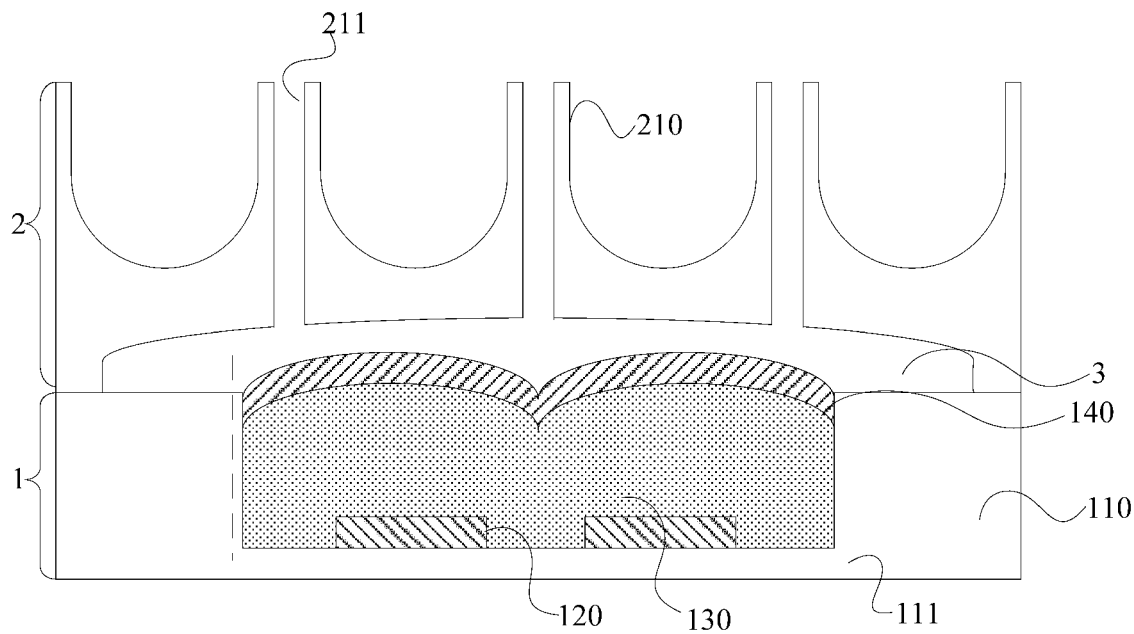

In some embodiments, by taking the micro-needle system illustrated in FIG. 5A as an example, when the micro-needle system is in a non-working state, no voltage is applied to the upper flexible electrode 140 and the bottom electrode 120, and at this time, there is no strain in the electro-active polymer layer 130 and the electro-active polymer layer 130 is in a flat state, therefore, no liquid will be driven into the micro-needle through-holes 211 to thereby enter the human skin. And as illustrated in FIG. 6A, when the micro-needle system is in a working state, a voltage is applied to the upper flexible electrode 140 and the bottom electrode 120, at this time, the electro-active polymer layer 130 may generate a strain and form a protrusion to thereby squeeze the liquid in the liquid storage region 3 to enter the human skin via the micro-needle through-holes 211. For example, as illustrated in FIG. 6B, as the voltage applied to the upper flexible electrode 140 and the bottom electrode 120 increases, the strain in the electro-active polymer layer 130 becomes larger and the protrusion formed thereof becomes more obvious, thereby the liquid in the liquid storage region 3 will be squeezed to enter the human skin via the micro-needle through-holes 211 continuously.

In some embodiments, when there are a plurality of bottom electrodes 120 in a groove, a strain amount of an electro-active polymer layer can be controlled by adjusting the number of the bottom electrodes applied with the electrical signal and the amplitude of the electrical signal, thereby accurately controlling the liquid amount entering a micro-needle through-hole. For example, in an initial stage, a certain bottom electrode 120 can be applied with an electrical signal from small to large, so that a continuous amount of deformation may occur at a corresponding position of the electro-active polymer layer 130; in a subsequent stage, when a maximum value of the electrical signal applied to the certain bottom electrode 120 is maintained, another bottom electrode 120 is applied with an electrical signal from small to large, so that a continuous amount of deformation occurs at a corresponding position of the electro-active polymer layer 130; and the above process is performed similarly until all the bottom electrodes 120 are applied with an electrical signal with the maximum value.

In some embodiments, in the micro-needle system above according to the embodiments of the disclosure, as illustrated in FIG. 5A to FIG. 5F, the micro-needle component 2 is further arranged with a groove at a side facing the drive component 1, and each liquid storage region 3 includes a corresponding groove of the micro-needle component 2. Further, when each upper flexible electrode 140 is lower than an upper surface of a corresponding groove 111 of the drive component 1, each liquid storage region 3 can further include a portion of a corresponding groove 111 of the drive component 1 above a corresponding upper flexible electrode 140.

Figure 7:
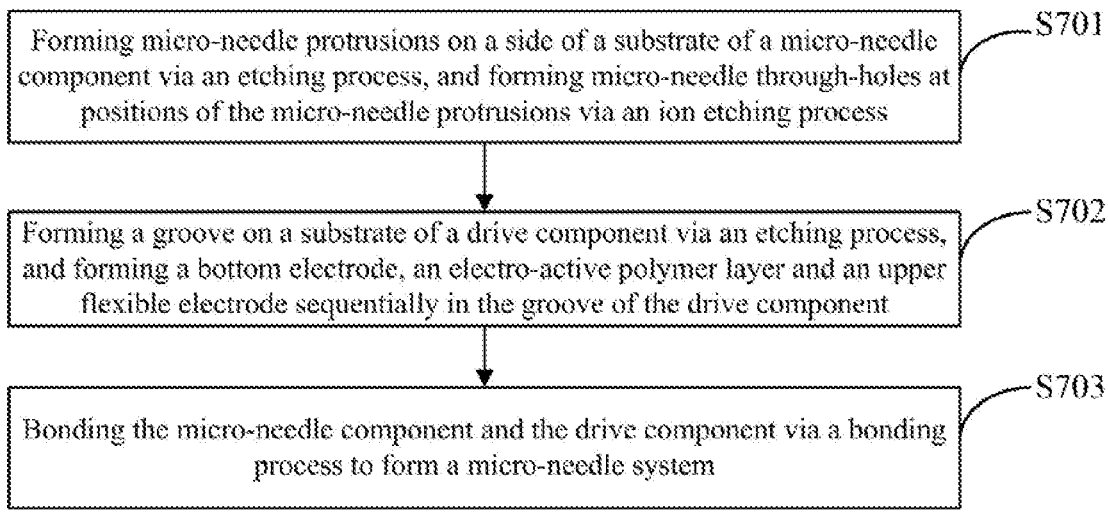
FIG. 7 is a flow chart of a method for fabricating a micro-needle system according to the embodiments of the disclosure.

Based upon the same inventive concept, the embodiments of the disclosure further provide a method for fabricating the micro-needle system, and as illustrated in FIG. 7, the method includes following operations.

In operation 701, forming micro-needle protrusions on a side of a substrate of a micro-needle component via an etching process, and forming micro-needle through-holes at positions of the micro-needle protrusions via an ion etching process.

In operation 702, forming a groove on a substrate of a drive component via an etching process, and forming a bottom electrode, an electro-active polymer layer and an upper flexible electrode sequentially in the groove of the drive component.

In operation 703, bonding the micro-needle component and the drive component via a bonding process to form a micro-needle system.

In some embodiments, in the method above for fabricating the micro-needle system according to the embodiments of the disclosure, the method can further include: forming a liquid storage region on the other side of the substrate of the micro-needle component via an etching process.

In some embodiments, respective operations in the method above for fabricating the micro-needle system according to the embodiments of the disclosure will be described below in detail by taking the micro-needle system illustrated in FIG. 5A as an example.

Where, as illustrated, forming the micro-needle component includes operations as follows.

Figure 8A:
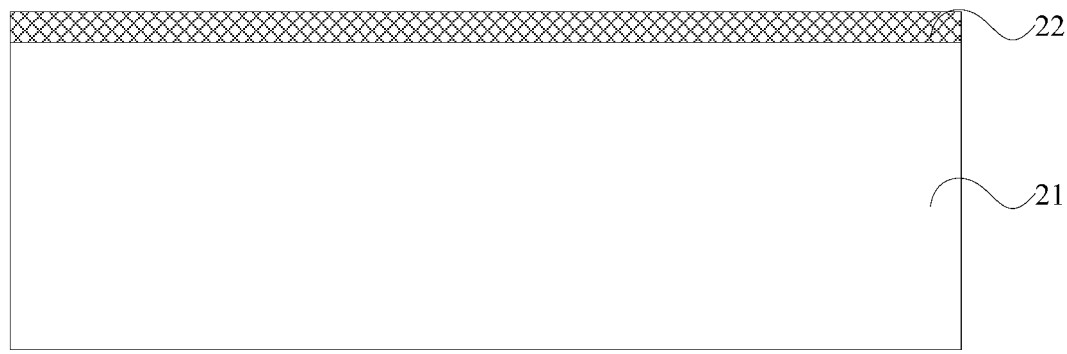
FIG. 8A to FIG. 8G are schematic diagrams of a process of fabricating a micro-needle component of a micro-needle system according to the embodiments of the disclosure.

Operation 1, coating a first photoresist 22 on a side of a provided Si substrate 21, as illustrated in FIG. 8A.

Figure 8B:

Operation 2, exposing and developing the first photoresist 22 to form a first photoresist pattern 221, as illustrated in FIG. 8B.

Figure 8C:
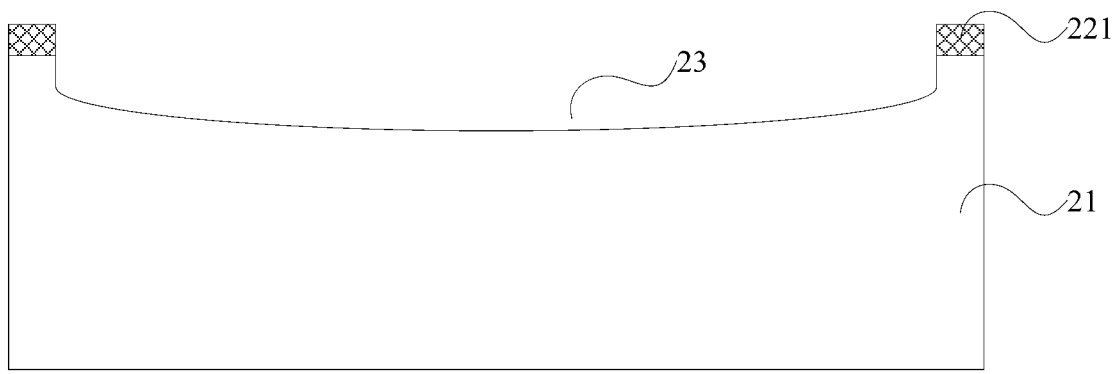

Operation 3, removing a partial portion of the Si substrate 21 via etching or the like to form a groove 23, as illustrated in FIG. 8C.

Figure 8D:
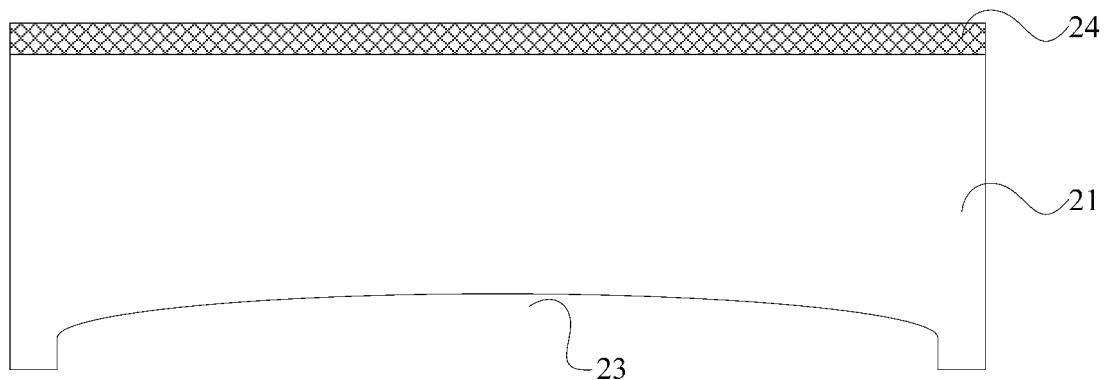

Operation 4, coating a second photoresist 24 on the other side of the Si substrate 21 after removing the first photoresist pattern 221, as illustrated in FIG. 8D.

Figure 8E:
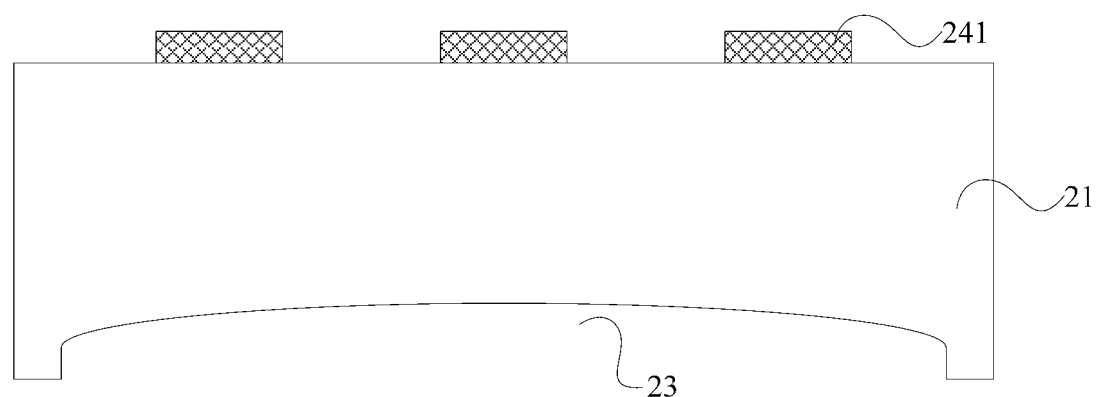

Operation 5, exposing and developing the second photoresist 24 to form a second photoresist pattern 241, as illustrated in FIG. 8E.

Figure 8F:
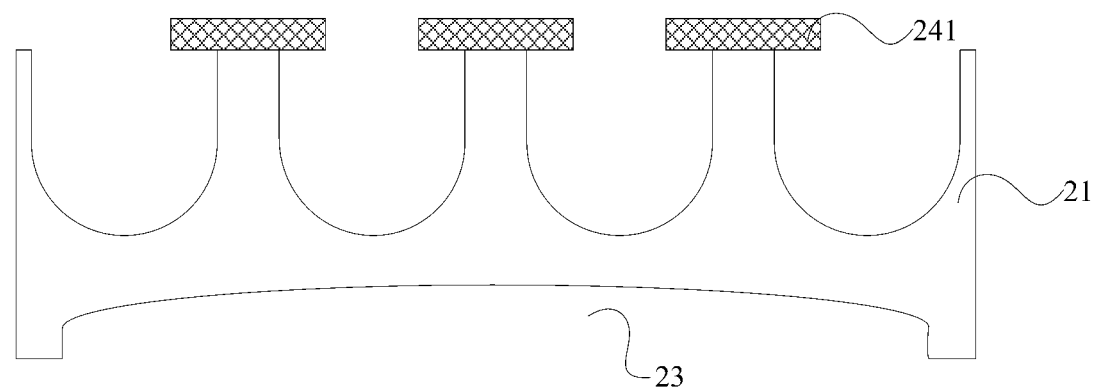

Operation 6, removing a partial portion of the Si substrate 21 via etching or the like to form micro-needle protrusions, as illustrated in FIG. 8F.

Figure 8G:
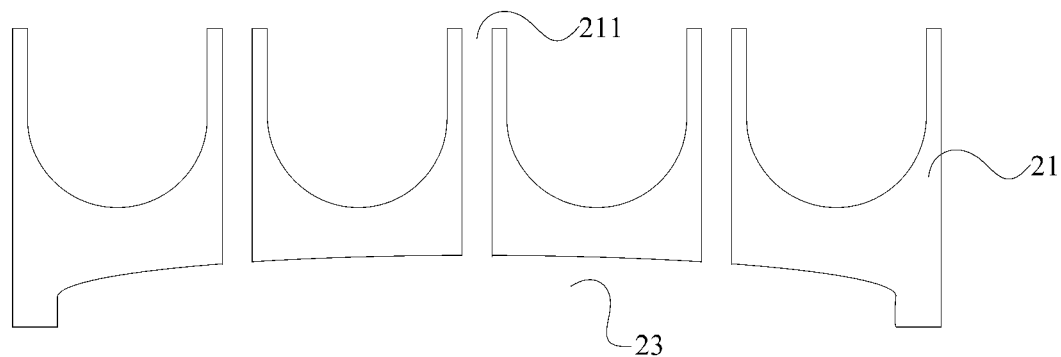

Operation 7, forming micro-needle through-holes 211 via a deep reactive ion etching process, after removing the second photoresist pattern 241, as illustrated in FIG. 8G.

In some embodiments, forming the drive component 2 includes operations as follows.

Figure 9A:
FIG. 9A to FIG. 9F are schematic diagrams of a process of fabricating a drive component of a micro-needle system according to the embodiments of the disclosure.

Operation 1, coating a third photoresist 10 on a side of a provided substrate 110, as illustrated in FIG. 9A.

Figure 9B:

Operation 2, exposing and developing the third photoresist 10 to form a third photoresist pattern 101, as illustrated in FIG. 9B.

Figure 9C:
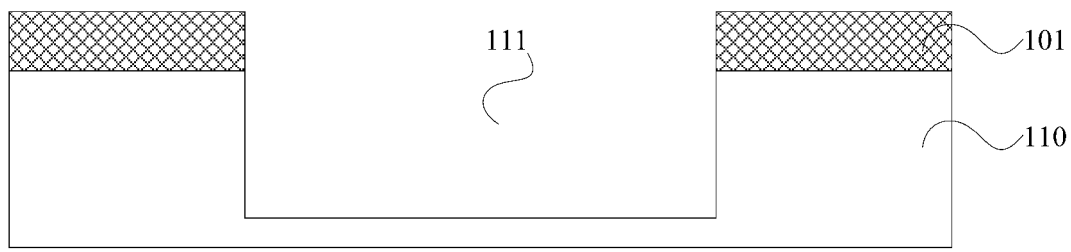

Operation 3, removing a partial portion of the substrate 110 via etching or the like to form a groove 111, as illustrated in FIG. 9C.

Figure 9D:
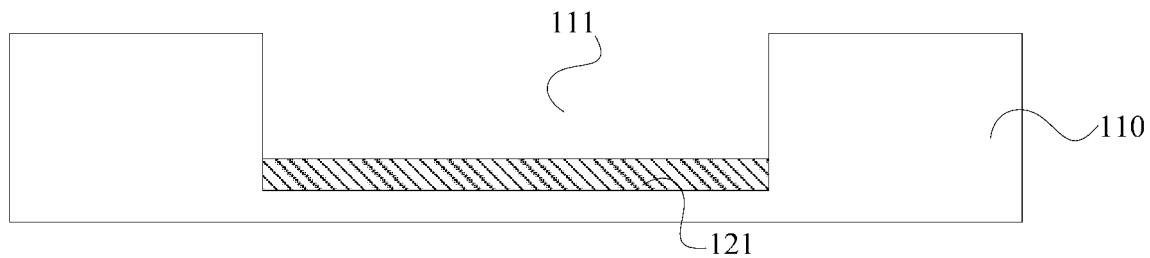

Operation 4, forming a bottom electrode film layer 121 in the groove 111 via a sputter process or the like after removing the third photoresist pattern 101, as illustrated in FIG. 9D.

Figure 9E:
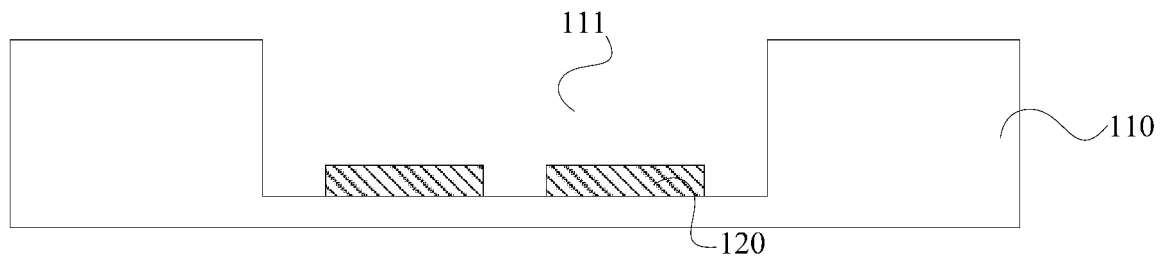

Operation 5, forming a pattern of a bottom electrode 120 via a patterning process, as illustrated in FIG. 9E.

Figure 9F:
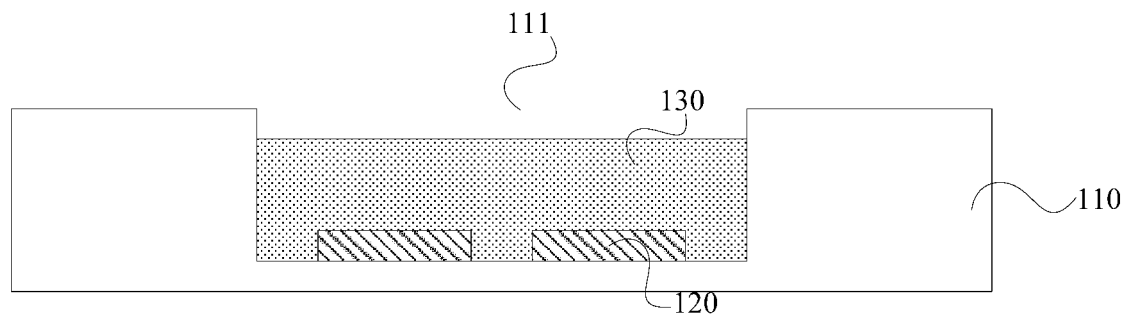

Operation 6, forming an electro-active polymer layer 130 via a process such as PECVD, as illustrated in FIG. 9F.

Operation 7, forming an upper flexible electrode 140 via a sputter process or the like, as illustrated in FIG. 3A.

In the drive component of the micro-needle system and the micro-needle system according to the embodiments of the disclosure, since an electro-active polymer material may generate a strain upon application of voltage, the electro-active polymer layer and the bottom electrode are arranged in the groove of the substrate, and the electro-active polymer layer is controlled by the voltage to generate a deformation to thereby change a shape of the upper flexible electrode covering the electro-active polymer layer and thus squeeze liquid in a liquid storage region into a micro-needle through-hole when the drive component is applied to a micro-needle system, thereby achieving the effect of driving the liquid into human skin by a driver, such as a micro-pump or a micro-valve, in the related art. And since the driving is achieved by controlling the electro-active polymer material to generate a deformation under the voltage, the problem in the related art that the MEMS devices, such as the cantilever-beam-type micro-valve, may be in firm contact with the substrate easily due to effects of electrostatic force, hydrogen bonding, Van Der Waals force and the like, thereby causing malfunction of the micro-needle system, can be avoided.

Evidently those skilled in the art can make various modifications and variations to the disclosure without departing from the spirit and scope of the disclosure. Accordingly the disclosure is also intended to encompass these modifications and variations thereto so long as the modifications and variations come into the scope of the claims appended to the disclosure and their equivalents.

The invention claimed is:

1. A drive component of a micro-needle system, comprising:
   a substrate with a groove;

a bottom electrode in the groove;
an electro-active polymer layer, covering the bottom electrode, in the groove; and
an upper flexible electrode covering the electro-active polymer layer;
wherein the upper flexible electrode and the bottom electrode are configured to generate a voltage, the electro-active polymer layer is configured to generate a strain under the voltage, the strain changes a shape of the upper flexible electrode;
wherein the bottom electrode is provided with:
a first surface; and
a second surface in opposition to the first surface;
wherein the first surface and the second surface are parallel to the substrate, the first surface is in contact with a bottom of the groove, and the second surface is in contact with the electro-active polymer layer.

2. The drive component according to claim 1, wherein the groove is arranged with a plurality of bottom electrodes arranged spaced apart from each other.

3. The drive component according to claim 1, wherein the upper flexible electrode only covers the groove.

4. The drive component according to claim 1, wherein the upper flexible electrode is flush with an upper surface of the groove.

5. The drive component according to claim 1, wherein a material of the electro-active polymer layer comprises a conductive polymer or an ionic polymer-based metal composite.

6. A micro-needle system, comprising a micro-needle component and a drive component fit tightly with each other;
wherein the micro-needle component comprises a plurality of micro-needle protrusions, each of which comprises a micro-needle through-hole;
the drive component comprises a substrate with a groove; a bottom electrode in the groove; an electro-active polymer layer, covering the bottom electrode, in the groove; and an upper flexible electrode covering the electro-active polymer layer; wherein the upper flexible electrode and the bottom electrode are configured to generate a voltage, and the electro-active polymer layer is configured to generate a strain under the voltage; and
a liquid storage region is arranged between respective micro-needle through-holes of the micro-needle component and the groove of the drive component, and the liquid storage region is at a side, facing away from the bottom electrode, of the upper flexible electrode.

7. The micro-needle system according to claim 6, wherein the micro-needle system comprises a plurality of liquid storage regions corresponding to and connected with the respective micro-needle through-holes in a one-to-one manner.

8. The micro-needle system according to claim 6, wherein the drive component comprises a plurality of grooves; and the upper flexible electrode is adjacent to the liquid storage region.

9. The micro-needle system according to claim 8, wherein each groove is arranged with a plurality of bottom electrodes arranged spaced apart from each other.

10. The micro-needle system according to claim 8, wherein the upper flexible electrode is arranged as a whole layer to cover each electro-active polymer layer in the plurality of grooves.

11. The micro-needle system according to claim 6, wherein the upper flexible electrode only covers the groove.

12. The micro-needle system according to claim 6, wherein the upper flexible electrode is flush with an upper surface of the groove.

13. The micro-needle system according to claim 6, wherein a material of the electro-active polymer layer comprises a conductive polymer or an ionic polymer-based metal composite.

14. The micro-needle system according to claim 6, wherein the micro-needle component is arranged with a groove on a side facing the drive component, and the liquid storage region comprises the groove of the micro-needle component.

15. A method for driving the drive component according to claim 1, comprising:
applying an electrical signal to the upper flexible electrode and the bottom electrode to generate a voltage to make the electro-active polymer layer generate a strain under the voltage.

16. A method for fabricating the micro-needle system according to claim 6, comprising:
forming the plurality of micro-needle protrusions on a side of a substrate of the micro-needle component via an etching process, and forming respective micro-needle through-holes at positions of the plurality of micro-needle protrusions via an ion etching process;
forming the groove on the substrate of the drive component via an etching process, and forming the bottom electrode, the electro-active polymer layer and the upper flexible electrode sequentially in the groove of the drive component; and
bonding the micro-needle component and the drive component via a bonding process to form the micro-needle system.

17. The drive component according to claim 1, wherein the upper flexible electrode covers an entire surface of the substrate.

18. The drive component according to claim 1, wherein the upper flexible electrode is lower than the upper surface of the groove.

19. The micro-needle system according to claim 6, wherein the micro-needle system comprises one liquid storage region connecting with the respective micro-needle through-holes.

20. The micro-needle system according to claim 6, wherein the upper flexible electrode is lower than the upper surface of the groove.

* * * * *